(12) United States Patent
Goral et al.

(10) Patent No.: US 10,028,691 B2
(45) Date of Patent: Jul. 24, 2018

(54) NEEDLE ASSEMBLY WITH DIAGNOSTIC ANALYSIS PROVISIONS

(71) Applicant: Smiths Medical ASD, Inc., Rockland, MA (US)

(72) Inventors: David Goral, Brookfield, CT (US); Harsh Chheda, Cheshire, CT (US); Jay Breindel, Branford, CT (US); Gursel Akcay, Madison, CT (US); James Muskatello, Southington, CT (US); David Justmann, Somerset, WI (US)

(73) Assignee: Smiths Medical ASD, Inc., Plymouth, MN (US)

( * ) Notice: Subject to any disclaimer, the term of this patent is extended or adjusted under 35 U.S.C. 154(b) by 264 days.

(21) Appl. No.: 15/012,059

(22) Filed: Feb. 1, 2016

(65) Prior Publication Data

US 2016/0220161 A1 Aug. 4, 2016

Related U.S. Application Data

(60) Provisional application No. 62/109,745, filed on Jan. 30, 2015, provisional application No. 62/109,722, (Continued)

(51) Int. Cl.
*A61B 5/15* (2006.01)
*A61M 21/02* (2006.01)
(Continued)

(52) U.S. Cl.
CPC .... *A61B 5/150824* (2013.01); *A61B 5/15003* (2013.01); *A61B 5/1535* (2013.01);
(Continued)

(58) Field of Classification Search
CPC .......... A61B 5/150824; A61B 5/15003; A61B 5/150221; A61B 5/150259; A61B 5/150732; A61B 5/1535; A61B 17/1325; A61B 25/0693; A61M 5/3202; A61M 5/422; A61M 21/02; A61M 25/0097; A61M 25/0631; A61M 25/0693; A61M 39/22; A61M 2021/0016; A61M 2205/0205
(Continued)

(56) References Cited

U.S. PATENT DOCUMENTS 3,298,789 A * 1/1967 Mast ........................ C12Q 1/54
435/14
3,692,490 A * 9/1972 Hall ......................... G01N 1/12
141/27
(Continued)

FOREIGN PATENT DOCUMENTS

WO  WO 8600513 A1 * 1/1986 ............... C12Q 1/54
WO  WO 03/043496 A2  5/2003

OTHER PUBLICATIONS

PCT Search Report dated May 17, 2016 for PCT Application No. PCT/US2016/015972, 14 pages.

*Primary Examiner* — Navin Natnithithadha
(74) *Attorney, Agent, or Firm* — Patterson Thuente Pedersen, P.A.

(57) ABSTRACT

A needle assembly. The needle assembly enabling the analysis of fluid trapped in a flashback chamber after an insertion needle has been inserted into a patient's vein.

15 Claims, 15 Drawing Sheets

Related U.S. Application Data filed on Jan. 30, 2015, provisional application No. 62/109,750, filed on Jan. 30, 2015, provisional application No. 62/109,742, filed on Jan. 30, 2015, provisional application No. 62/109,710, filed on Jan. 30, 2015, provisional application No. 62/109,766, filed on Jan. 30, 2015, provisional application No. 62/109,715, filed on Jan. 30, 2015, provisional application No. 62/109,759, filed on Jan. 30, 2015, provisional application No. 62/109,735, filed on Jan. 30, 2015, provisional application No. 62/109,755, filed on Jan. 30, 2015, provisional application No. 62/109,673, filed on Jan. 30, 2015.

(51) Int. Cl.

| | | |
|---|---|---|
| *A61M 39/22* | (2006.01) | |
| *A61M 25/06* | (2006.01) | |
| *A61M 25/00* | (2006.01) | |
| *A61M 5/32* | (2006.01) | |
| *A61M 5/42* | (2006.01) | |
| *A61B 5/153* | (2006.01) | |
| *A61B 17/132* | (2006.01) | |
| *A61M 21/00* | (2006.01) | |

(52) U.S. Cl.
CPC .. *A61B 5/150221* (2013.01); *A61B 5/150259* (2013.01); *A61B 5/150732* (2013.01); *A61M 5/3202* (2013.01); *A61M 5/422* (2013.01); *A61M 21/02* (2013.01); *A61M 25/0097* (2013.01); *A61M 25/0631* (2013.01); *A61B 17/1325* (2013.01); *A61M 25/0693* (2013.01); *A61M 39/22* (2013.01); *A61M 2021/0016* (2013.01); *A61M 2205/0205* (2013.01)

(58) Field of Classification Search
USPC .......................................... 600/309, 345–366
See application file for complete search history.

(56) References Cited

U.S. PATENT DOCUMENTS

| | | | |
|---|---|---|---|
| 5,000,740 A | | 3/1991 | Ducharme |
| 5,007,901 A | | 4/1991 | Shields |
| 5,114,678 A | * | 5/1992 | Crawford ................ B01L 3/505 |
| | | | 422/500 |
| 5,201,324 A | * | 4/1993 | Swierczek ......... A61B 5/15117 |
| | | | 600/583 |
| 5,368,029 A | | 11/1994 | Holcombe |
| 5,401,250 A | | 3/1995 | Shields |
| 5,438,984 A | * | 8/1995 | Schoendorfer .... A61B 5/14521 |
| | | | 600/346 |
| 5,441,048 A | * | 8/1995 | Schoendorfer .... A61B 5/14521 |
| | | | 600/346 |
| 5,465,713 A | * | 11/1995 | Schoendorfer ........ A61B 5/411 |
| | | | 600/346 |
| 5,638,815 A | * | 6/1997 | Schoendorfer .... A61B 5/14521 |
| | | | 600/346 |
| 5,685,855 A | | 11/1997 | Erskine |
| 5,817,011 A | * | 10/1998 | Schoendorfer .... A61B 5/14521 |
| | | | 600/362 |
| 5,817,012 A | * | 10/1998 | Schoendorfer .... A61B 10/0035 |
| | | | 600/362 |
| 5,919,356 A | | 7/1999 | Hood |
| 5,944,662 A | * | 8/1999 | Schoendorfer .... A61B 5/14521 |
| | | | 600/362 |
| 6,126,641 A | | 10/2000 | Shields |
| 6,547,762 B1 | | 4/2003 | Botich et al. |
| 6,603,987 B2 | * | 8/2003 | Whitson ............ A61B 5/14514 |
| | | | 422/550 |
| 7,125,396 B2 | | 10/2006 | Leinsing |
| 7,291,130 B2 | | 11/2007 | Mcgurk |
| 7,662,110 B2 | | 2/2010 | Flaherty |
| 7,736,342 B2 | | 6/2010 | Abriles |
| 7,785,299 B2 | | 8/2010 | Crawford et al. |
| 7,914,488 B2 | | 3/2011 | Dickerson |
| 8,249,681 B2 | * | 8/2012 | Rabinovitz ............ A61B 1/041 |
| | | | 600/309 |
| 8,257,322 B2 | | 9/2012 | Koehler |
| 8,383,044 B2 | | 2/2013 | Davis |
| 8,597,252 B2 | | 12/2013 | Burkholz |
| 8,721,546 B2 | | 5/2014 | Belson |
| 8,728,038 B2 | | 5/2014 | Spearman |
| 8,747,333 B2 | | 6/2014 | Burkholz |
| 8,986,227 B2 | | 3/2015 | Belson |
| 9,241,663 B2 | * | 1/2016 | Jena .................. G01N 21/8483 |
| 2004/0116830 A1 | | 6/2004 | Trudeau |
| 2004/0133090 A1 | * | 7/2004 | Dostoinov ............. A61F 13/42 |
| | | | 600/362 |
| 2005/0273019 A1 | | 12/2005 | Conway et al. |
| 2008/0146896 A1 | * | 6/2008 | Rabinowitz ............ A61B 1/041 |
| | | | 600/309 |
| 2012/0016265 A1 | | 1/2012 | Peterson |
| 2012/0016266 A1 | | 1/2012 | Burkholz |
| 2012/0101440 A1 | | 4/2012 | Kamen |
| 2013/0121897 A1 | | 5/2013 | Davis |
| 2014/0052021 A1 | | 2/2014 | Burkholz |
| 2014/0072189 A1 | * | 3/2014 | Jena .................. G01N 21/8483 |
| | | | 382/128 |
| 2014/0187892 A1 | | 7/2014 | Gupta |
| 2014/0188002 A1 | | 7/2014 | Close |
| 2014/0188003 A1 | | 7/2014 | Belson |
| 2014/0342461 A1 | * | 11/2014 | Resh .................. G01N 33/182 |
| | | | 436/125 |
| 2014/0357971 A1 | * | 12/2014 | Eilat .................. G01N 33/558 |
| | | | 600/362 |
| 2016/0220762 A1 | | 8/2016 | Goral et al. |
| 2016/0220791 A1 | | 8/2016 | Akcay et al. |
| 2016/0220805 A1 | | 8/2016 | Goral et al. |

\* cited by examiner

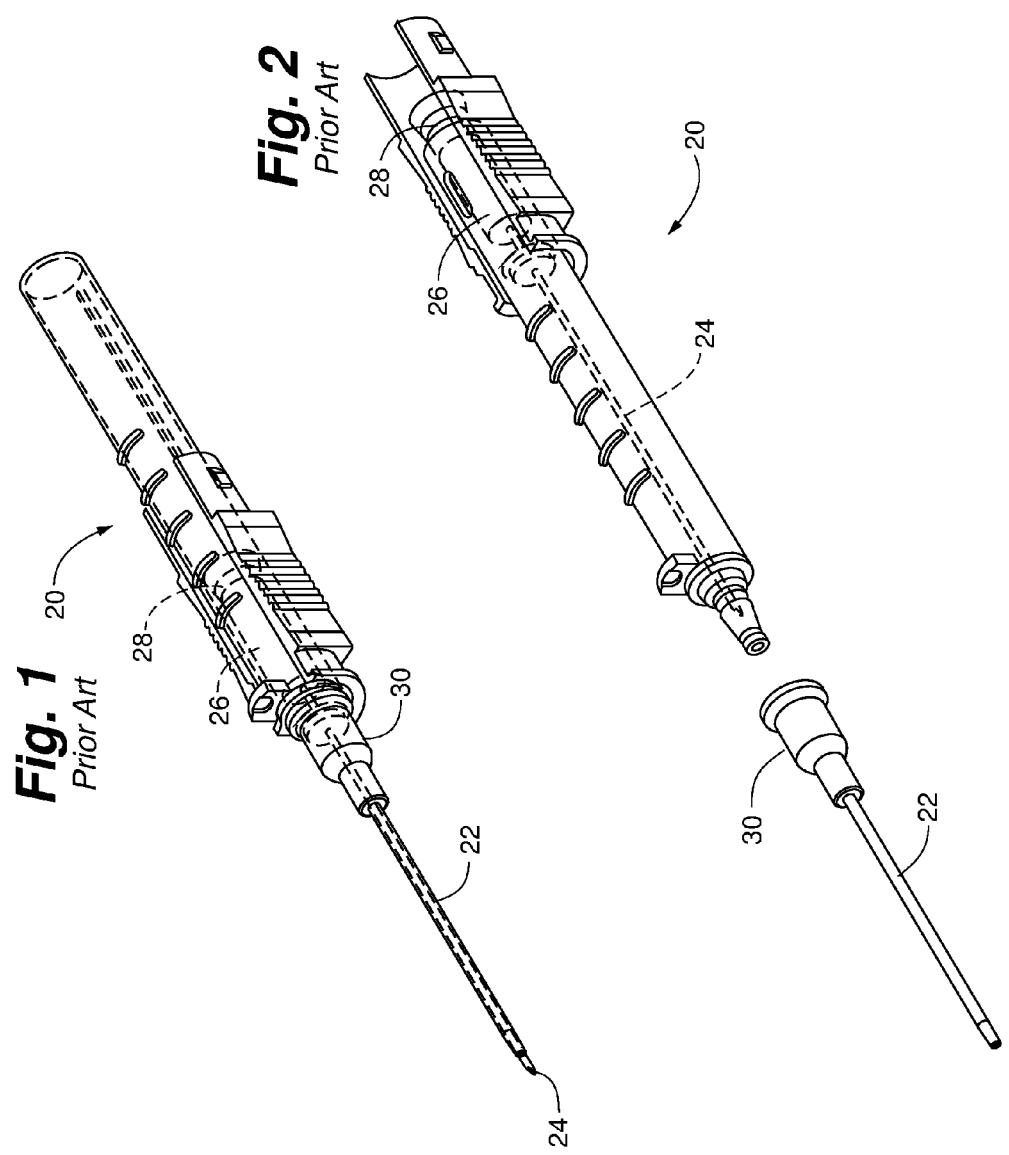

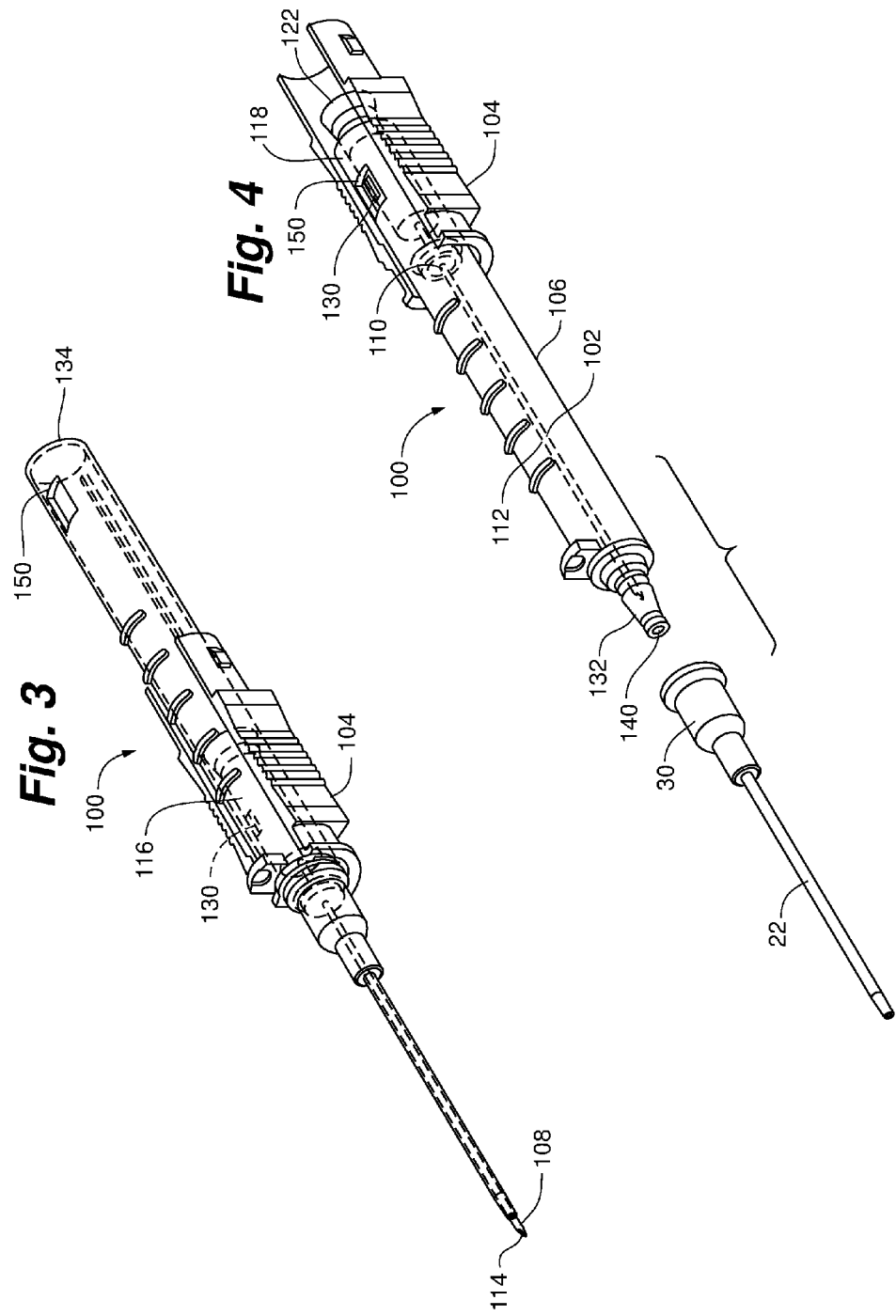

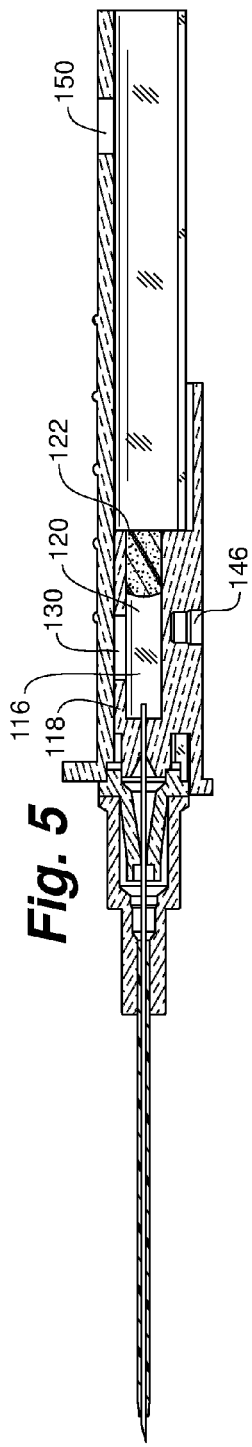
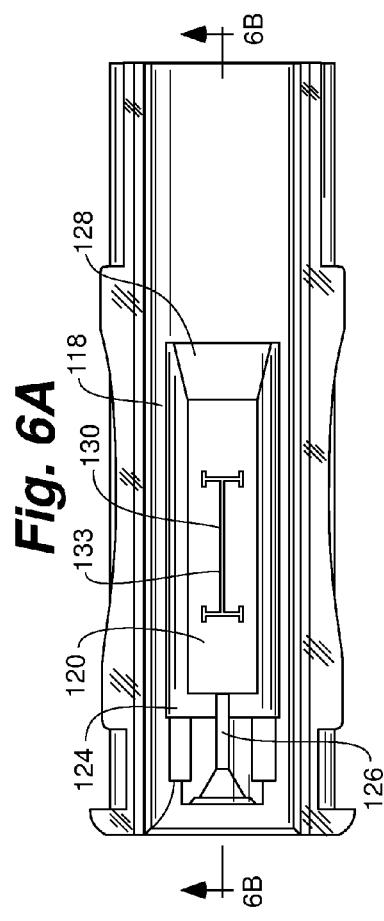
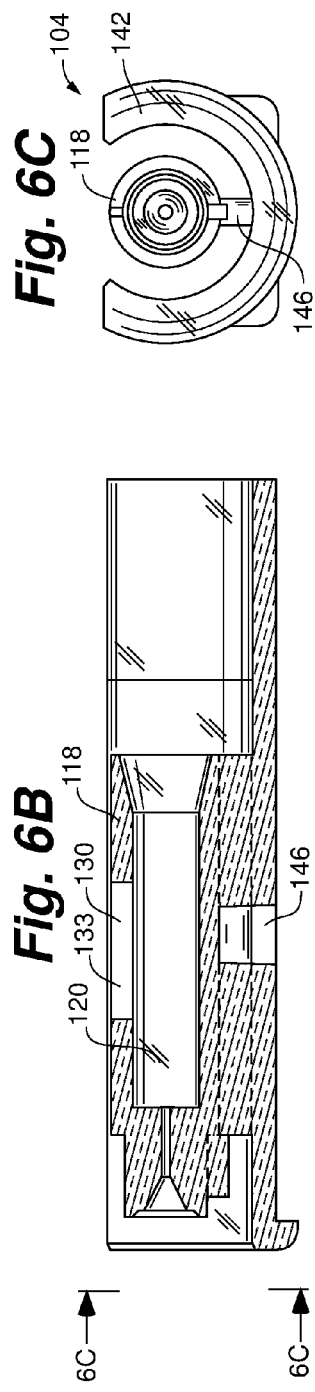
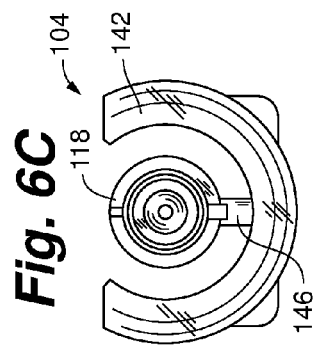

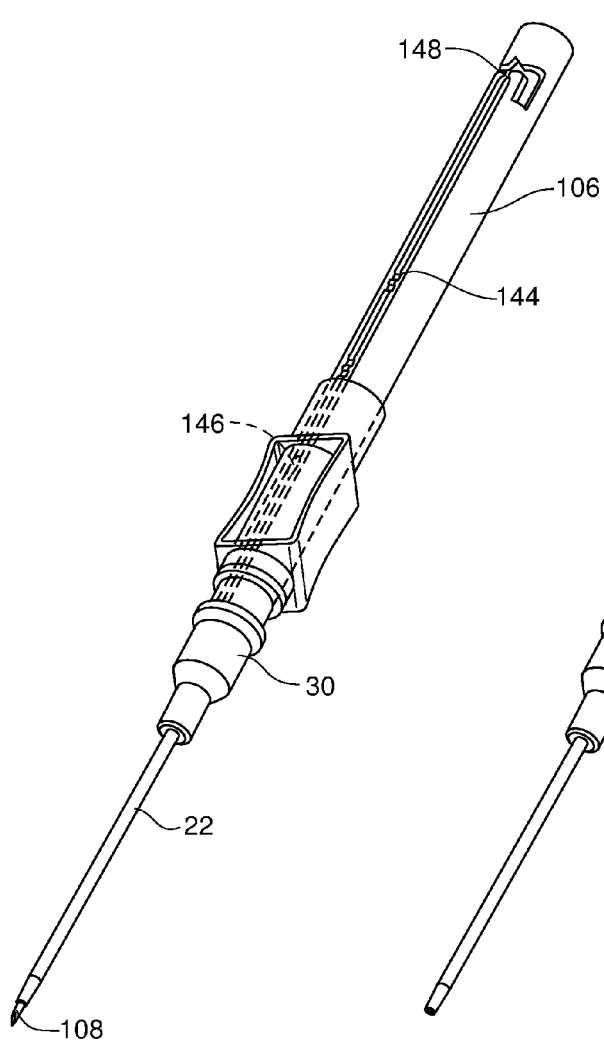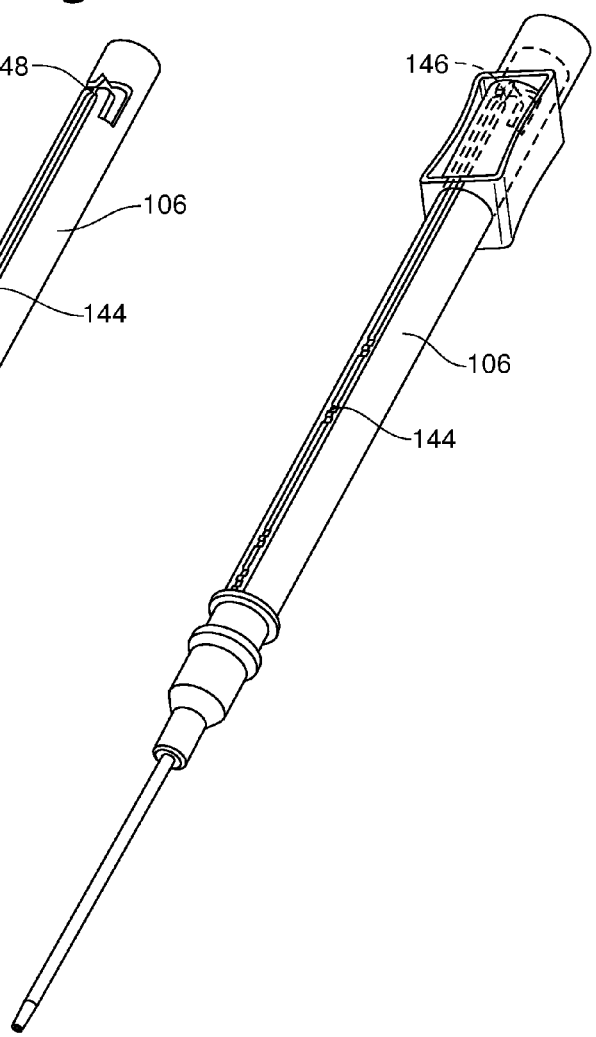

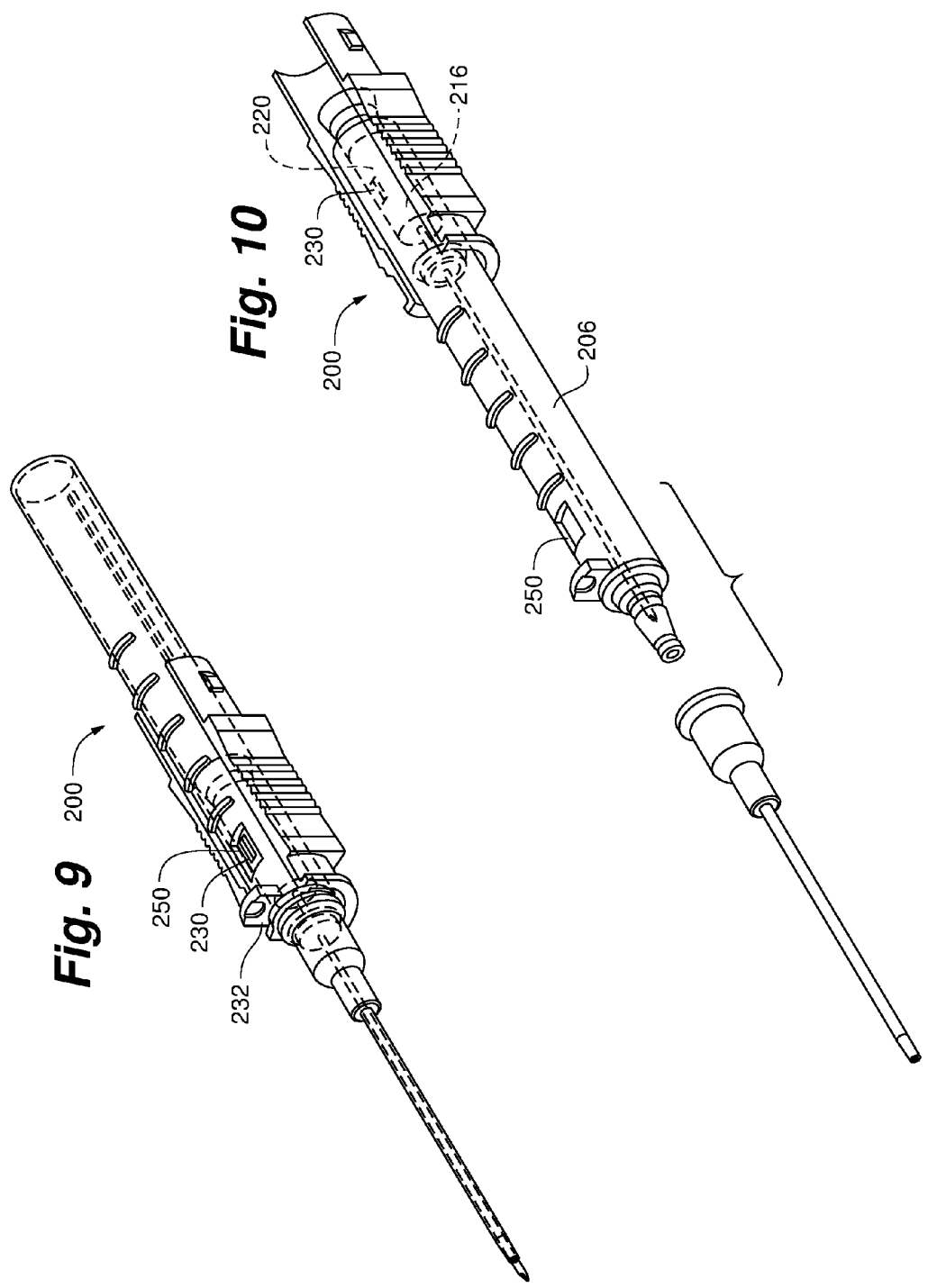

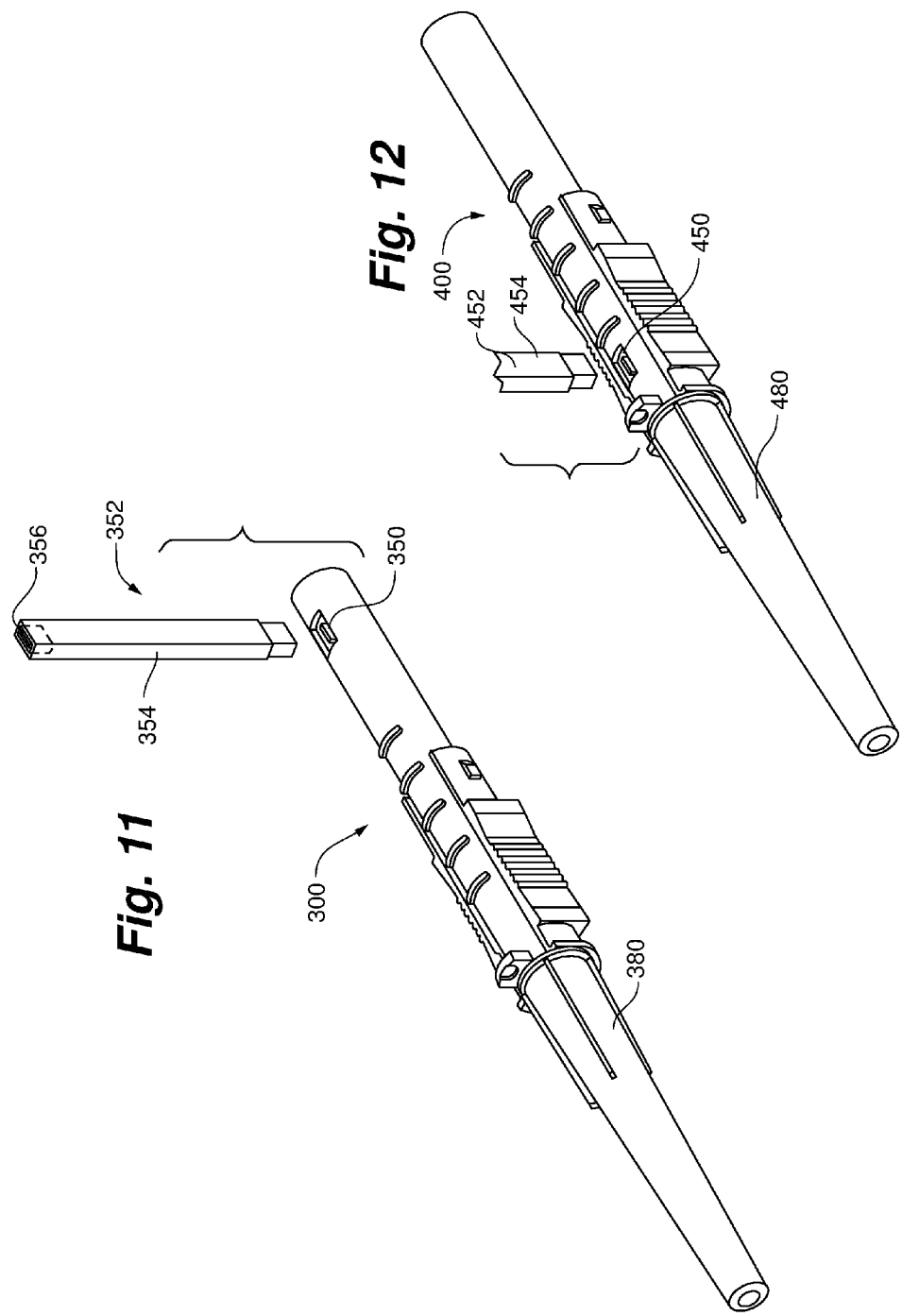

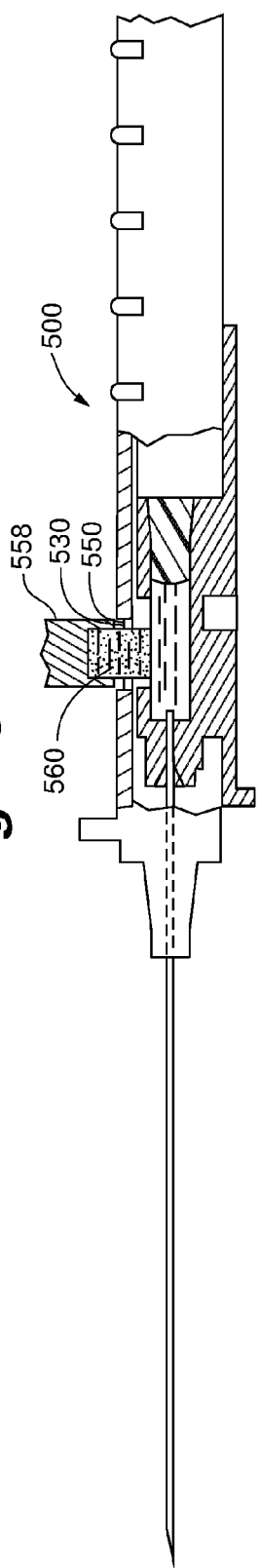
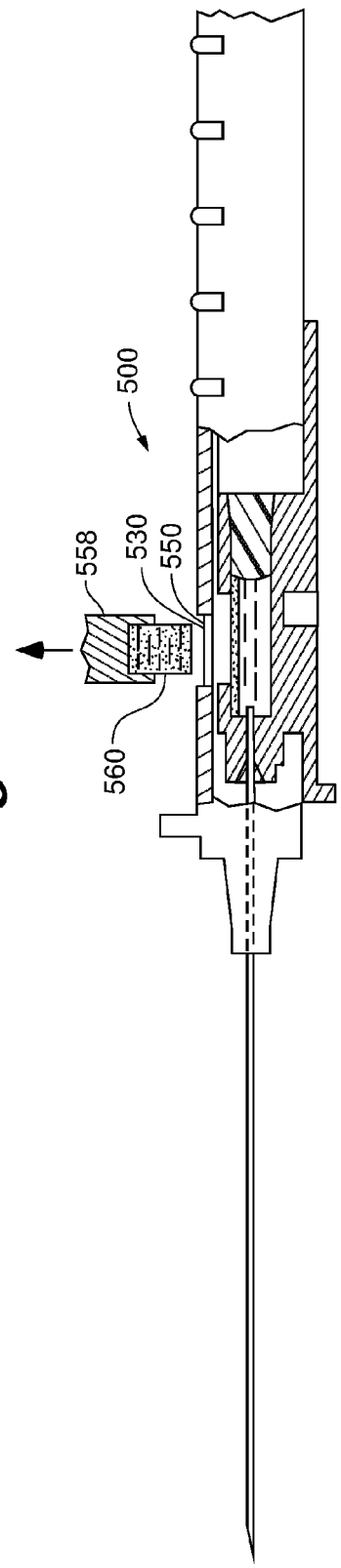

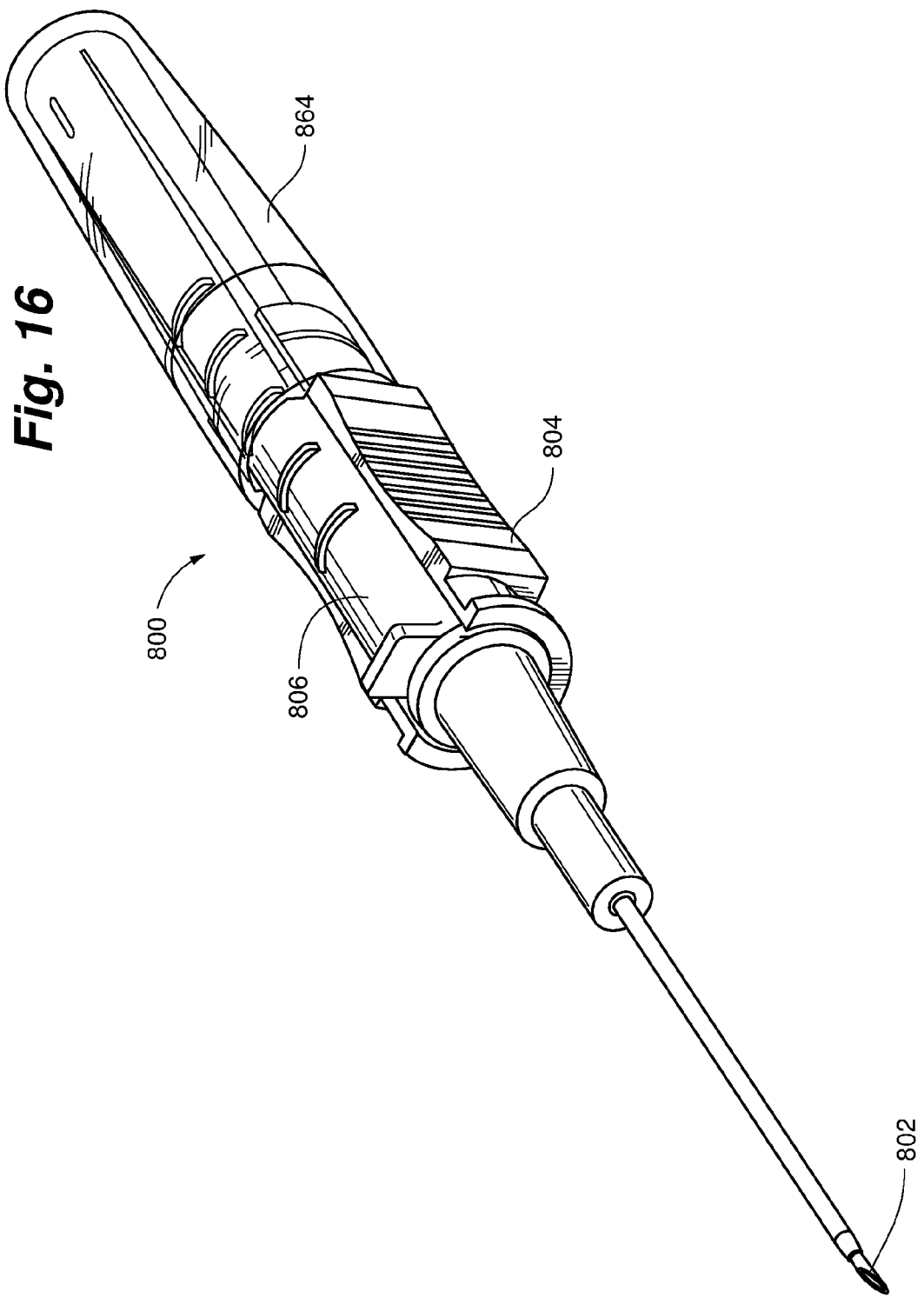

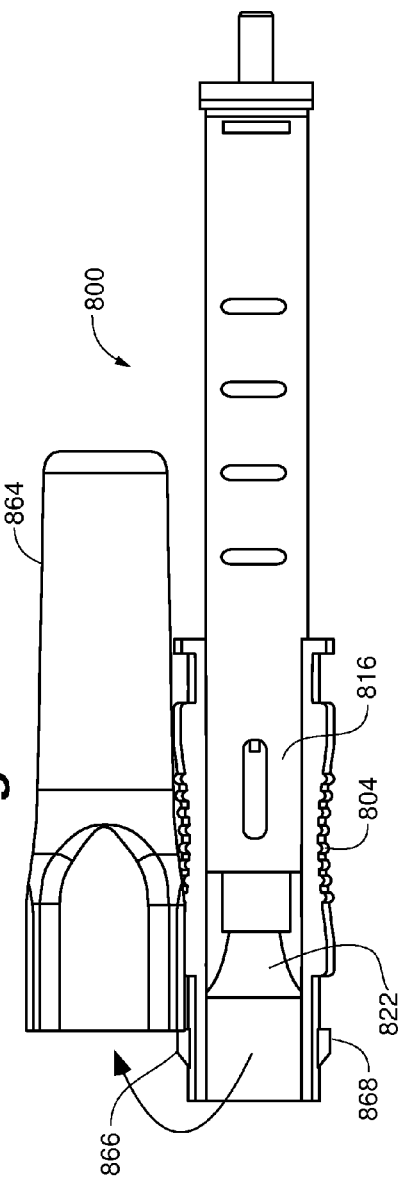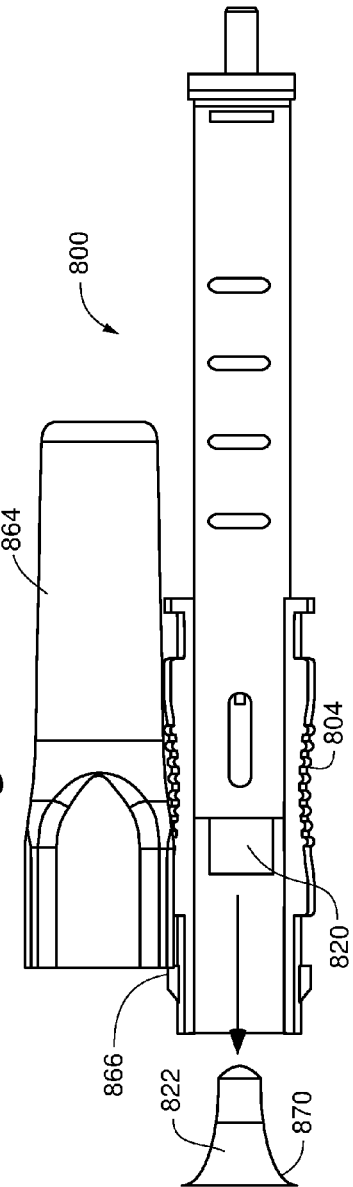

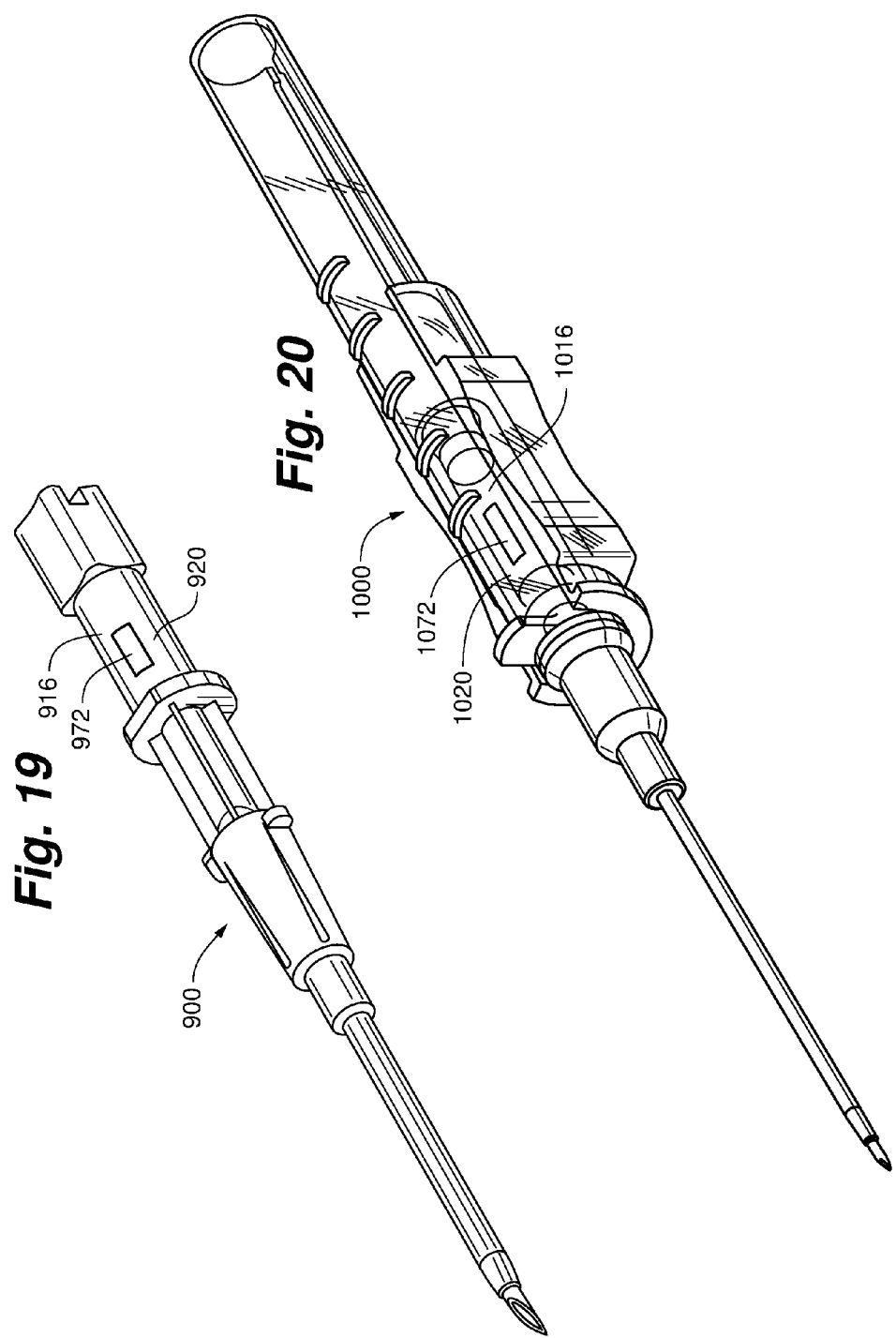

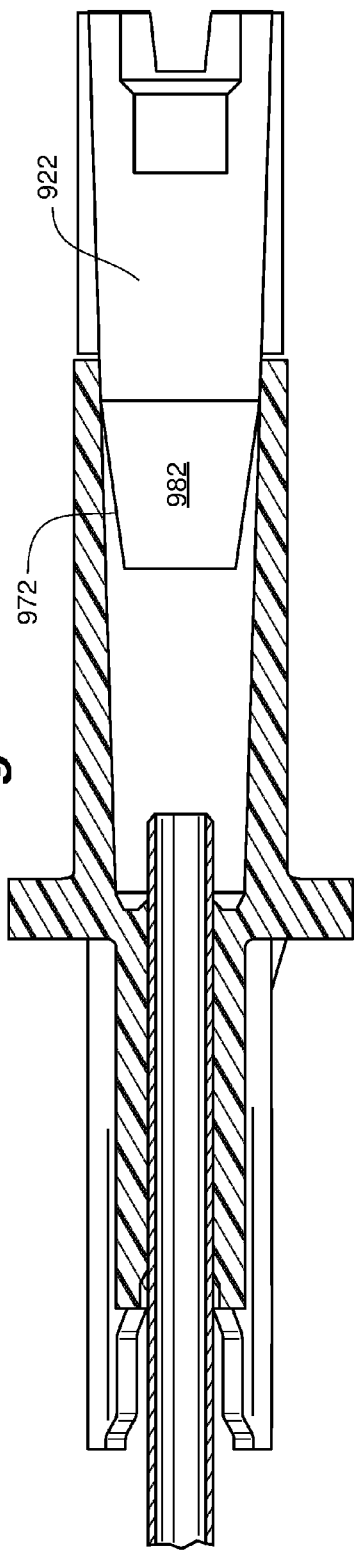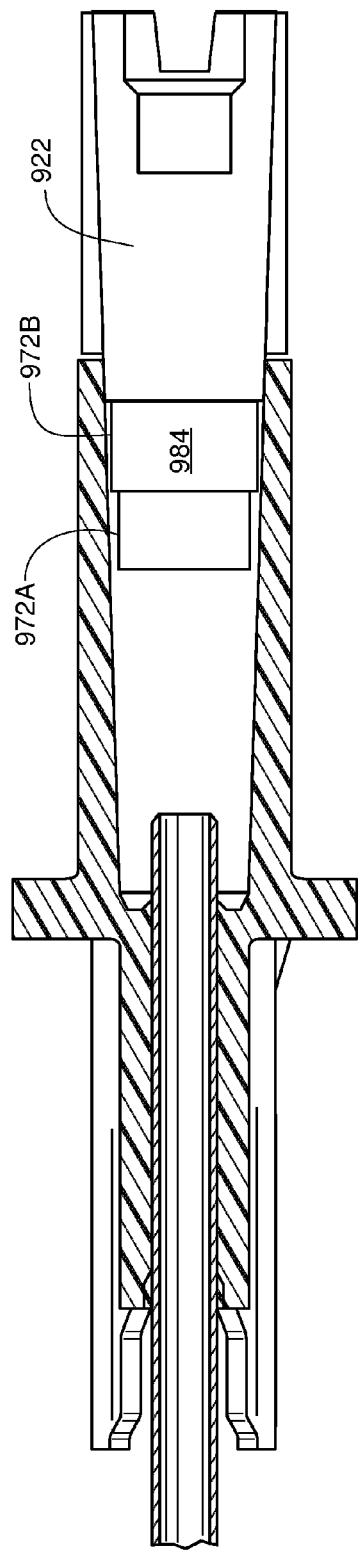

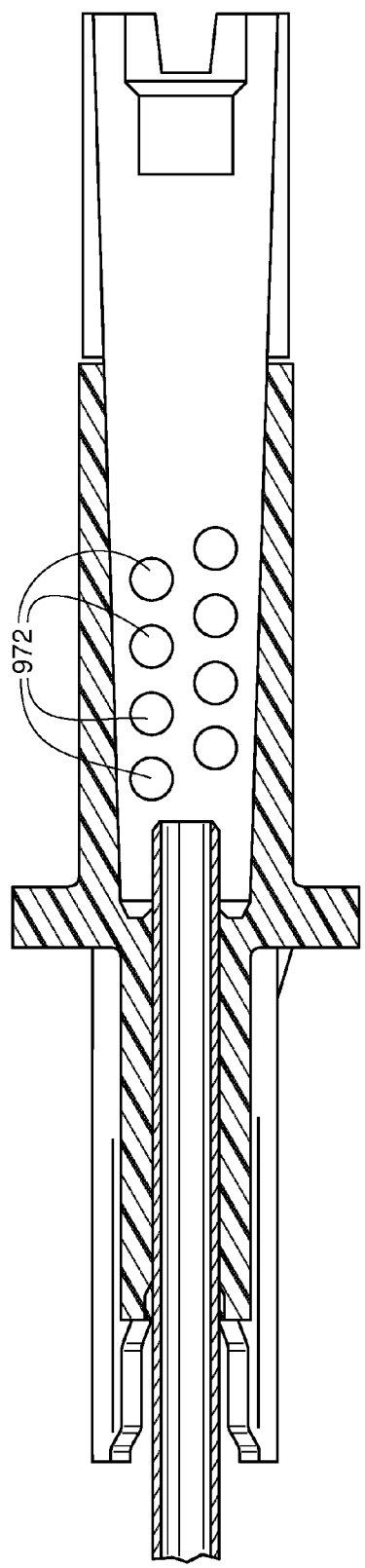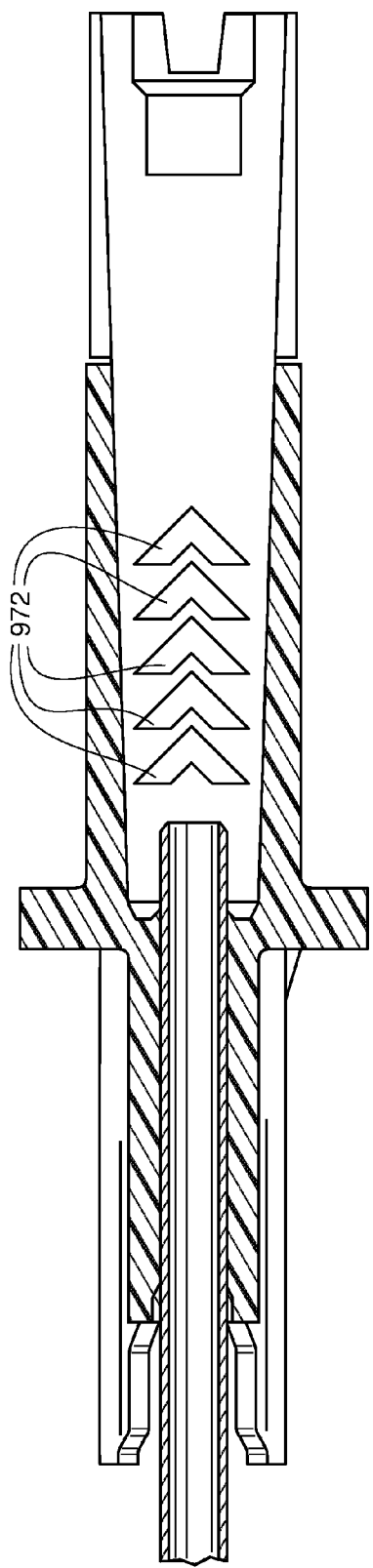

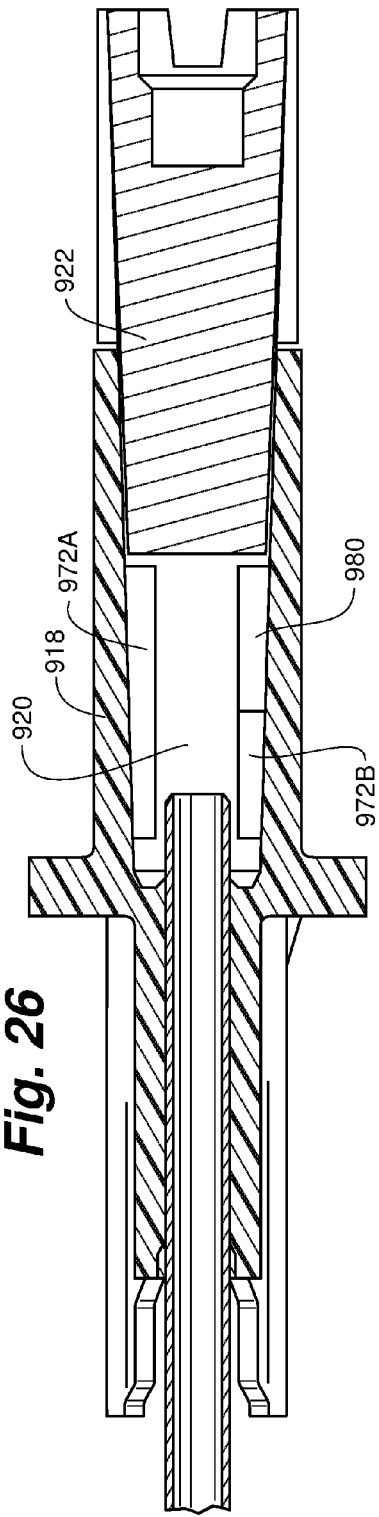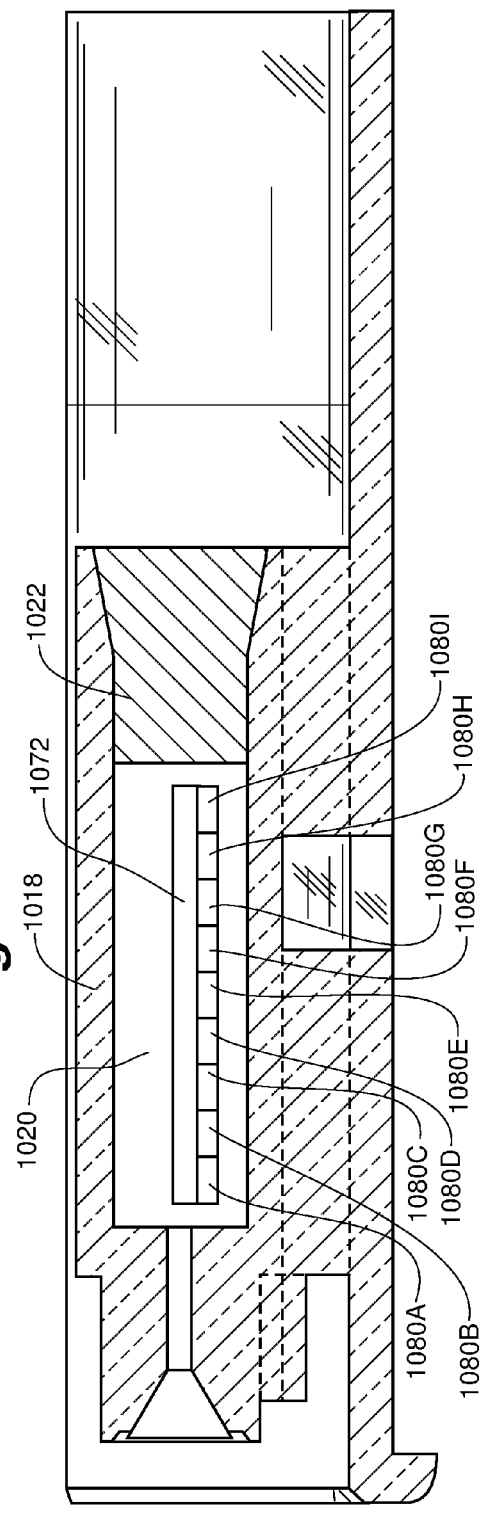

NEEDLE ASSEMBLY WITH DIAGNOSTIC ANALYSIS PROVISIONS

RELATED APPLICATIONS

The present application claims the benefit of U.S. Provisional Application Nos. 62/109,673; 62/109,710; 62/109,715; 62/109,722; 62/109,735; 62/109,742; 62/109,745; 62/109,750; 62/109,755; 62/109,759; 62/109,766, all of which were filed Jan. 30, 2015 and are hereby incorporated herein by reference.

TECHNICAL FIELD

The present disclosure relates generally to needle assemblies, and more particularly to a needle assembly having diagnostic sampling provisions to enable the testing and analysis of fluid captured by the needle assembly after needle insertion.

BACKGROUND

Intravenous (IV) therapy is a versatile technique used for the administration of medical fluids to and withdrawal of bodily fluids from patients. IV therapy has been used for various purposes such as the maintenance of fluid and electrolyte balance, the transfusion of blood, the administration of nutritional supplements, chemotherapy, and the administration of drugs and medications. Fluids may be administered intravenously by injection through a hypodermic needle, or intermittently or continuously by infusion using a needle or catheter. The most common intravenous access method utilized by clinicians is the peripheral IV catheter.

A peripheral IV catheter is made of soft, flexible plastic or silicone, generally between fourteen to twenty-four gauge in size. In the conventional venipuncture procedure, a catheter is inserted into a vein in the patient's hand, foot, or the inner aspect of the arm or any vein in the body that will accept an IV catheter. In order to properly place the IV catheter into a patient's vein, a sharp introducer needle must be used to puncture the skin, tissue, and vein wall to provide a path for placement of the catheter into the vein.

Referring to FIGS. 1 and 2, a conventional IV safety needle assembly 20 configured for insertion of an "over-the-needle" catheter 22 is depicted. The catheter 22 is operably coupleable to the safety needle assembly 20, in part by positioning the catheter 22 coaxially over the needle 24 of the safety needle assembly 20. The catheter 22 thus rides with the needle 24 through the skin, tissue, and vein wall and into the patient's vein. Often, the insertion end of the catheter 22 is tapered in an effort to minimize the amount of force required to insert catheter 22 into the biological site.

The catheter 22 can include a catheter hub 30, which can be selectively coupled to a portion of the safety needle assembly 20. Catheter hub 30 is sometimes configured to control the flow of fluid through catheter 22 via an internal fluid passageway that runs substantially parallel to the longitudinal axis of catheter hub 30. In some embodiments, the fluid passageway includes a septum or valve to enable sealing of the fluid passageway to restrict or prevent bodily fluid from leaking out of catheter hub 30 when catheter 22 is inserted into a patient's vein and the needle 24 is removed. Various catheter hub designs having a septum and/or valve are disclosed in a concurrently filed application entitled "Intravenous Catheter Assembly Design," Ser. No. 15/011,981, which is incorporated by reference herein.

When the needle 24 pierces the vein, blood will "flashback" through the needle 24 and into the flashback chamber 26. Thus, once the clinician observes this flashback of blood, the clinician will know that the catheter 22 and needle 24 have been inserted in the vein. The catheter 22 can be advanced further into the vein as desired and needle 24 can then be withdrawn from the catheter 22.

In addition to placement of an IV catheter, it is frequently necessary for a sample of the patient's blood to be obtained (e.g., for testing, blood typing or other analysis of a patient's condition). Such analysis frequently involves testing the blood for the presence of certain characteristics, such as the presence or amount of one or more constituents, or to determine the level of one or more than one parameter. For many of these blood tests, only a small sample of blood is required. After the IV catheter has been inserted, the clinician may obtain a blood sample through a variety of methods. One method is to have the patient endure another needle stick either by a needle and syringe to draw an aliquot of blood, or by pricking the patient's finger with a lancet for a few drops of blood.

Because some IV catheters of the prior art include an integrated flash chamber 26, another method is to enable access to the blood within the flash chamber 26 after the catheter 22 and needle 24 have been inserted into the patient's vein. Usually the proximal end of the flash chamber 26 is blocked by a flash plug 28. The flash plug 28 typically includes a filter material that enables air to vent from the flash chamber as the blood or fluid fills the chamber, but inhibits the blood or fluid from passing from the flash chamber 26.

In some IV catheters, the flash plug 28 is removable. Examples of catheter insertion devices incorporating removable plugs are marketed by Smiths Medical ASD, Inc. of St. Paul, Minn., under the JELCO and INTUITIV Safety IV Catheters trademarks, as described by U.S. Pat. Nos. 7,291,130 and 8,257,322, both of which are incorporated by reference herein. With this type of catheter, removal of the flash plug 28 opens the flash chamber 26, thereby providing access to the blood within the flash chamber 26 for testing. Although advantageous in some regards, this action has the potential to expose clinicians to hazardous material if improperly handled, such as blood or other bodily fluid that may spill from the flash chamber 26 as the plug 28 is removed.

In other IV catheters of the prior art, the flash plug 28 is fixed or non-removable. Examples of catheter insertion devices incorporating non-removable plugs are described in U.S. Pat. No. 5,000,740 (depicting an IV catheter insertion device marketed by Smiths Medical ASD, Inc. under the PROTECTIV trademark) and U.S. Pat. No. 7,736,342 (depicting an IV catheter insertion device marketed by Smiths Medical ASD, Inc. under the VIAVALVE trademark), both of which are incorporated by reference herein.

With non-removable flash plugs 28, clinicians must adapt special methods if they wish to access the blood within the flash chamber 26. One such method to access blood with a non-removable flash plug involves finding and using an external probe, such as a pen, to push the flash plug 28 within the flash chamber 26 to expel blood from the flash chamber 26 through the needle 24. The use of an external device such as a pen can be undesirable for several reasons. In particular, it is cumbersome in that it requires that the clinician find a pen or similar object, and use both hands to access the blood within the flash chamber 26. It increases the risk that the pen or other object, which may not be sterile, if improperly handled, will contaminate the blood and cause inaccuracies in the following tests. And, if improperly handled, it increases the risk that the pen itself will become contaminated from the blood within flash chamber 26, thereby putting the clinician and other patients at risk of making contact with trace amounts of the blood.

Accordingly, the applicants have identified a need for a better way of accessing and testing fluid trapped in a flashback chamber of a needle assembly in a manner that reduces the risk of the fluid spilling, while reducing the possibility of an inadvertent needle stick.

SUMMARY OF THE DISCLOSURE

Embodiments of the present disclosure meet the need for providing a better way of accessing and testing the fluid trapped in the flashback chamber of a needle assembly in a manner that reduces or eliminates the risk of the fluid spilling, while reducing the possibility of an inadvertent needle stick.

One embodiment of the present disclosure provides a safety needle assembly that enables access to fluid trapped in the flashback chamber after the insertion needle has been safely housed, thereby reducing the risk of an inadvertent needle stick. In addition, the risk of the fluid spilling is greatly reduced, as the fluid is tested by inserting a test strip directly into the flashback chamber via a diagnostic sampling port. This embodiment includes an insertion needle, a needle hub and a needle housing. The insertion needle has a sharpened distal tip, a proximal end and a shaft defining a lumen extending therebetween. The needle hub is operably coupled to the proximal end of the insertion needle. The needle hub includes a flash chamber comprising a wall defining a cavity in fluid communication with the lumen of the insertion needle and sealed at one end by a gas permeable flash plug. The cavity defining wall further includes structure defining a diagnostic sampling port configured to enable selective access to the cavity. The needle housing is slideably coupled to the needle hub, and is moveable between a first position wherein the sharpened distal tip extends from the needle housing, and a second position wherein the sharpened distal tip is housed within the needle housing. The needle housing includes structure defining an access port that aligns with the diagnostic sampling port when the needle housing is in one of the first position and the second position.

In some versions, the safety needle assembly further includes a catheter having a catheter hub coupleable to the needle housing when the needle housing is in the first position. In some versions, the gas permeable flash plug enables gas to vent from the flash chamber as fluid fills the cavity. In some versions, the diagnostic sampling port and the access port are sized to accommodate a standard sized blood glucose test strip. In some versions, the structure defining the diagnostic sampling port comprises a self-sealing member configured to re-seal the cavity after the cavity has been accessed through the diagnostic sampling port. In some versions, an interior surface of the wall defining the cavity is coated with a fluid integrity preserving substance. In some versions, the fluid integrity preserving substance is heparin.

Another embodiment of the present disclosure provides a safety needle assembly that enables a user to access fluid trapped in the flashback chamber via a hinged end cap that pivots to enable removal of the flash plug from the flashback chamber. This embodiment includes an insertion needle, a needle hub, an end cap, and a needle housing. The insertion needle has a sharpened distal tip, a proximal end and a shaft defining a lumen extending therebetween. The needle hub is operably coupled to the proximal end of the insertion needle. The needle hub includes a flash chamber comprising a wall defining the cavity in fluid communication with the lumen of the insertion needle and sealed at one end by a removable gas permeable flash plug. The end cap is hingedly coupled to the needle hub and is moveable between a closed position wherein the end cap covers the cavity sealing flash plug, and an open position wherein the end cap pivots to enable removal of the flash plug from the cavity. The needle housing is slideably coupled to the needle hub, and is moveable between a first position wherein the sharpened distal tip extends from the needle housing and the needle housing is at least partially housed within the end cap, and a second position wherein the sharpened distal tip is housed within the needle housing and the end cap extends from the needle housing.

In some versions, the safety needle assembly further includes a catheter having a catheter hub coupleable to the needle housing when the needle housing is in the first position. In some versions, the flash plug enables gas to vent from the flash chamber as fluid fills the cavity. In some versions, when the needle housing is in the first position, the needle housing at least partially secures the end cap in the closed position by inhibiting the end cap from pivoting. In some versions, the end cap further includes a latch to at least partially secure the end cap in the closed position. In some versions, the gas permeable flash plug includes a gripping surface to aid in the removal of the flash plug from the cavity. In some versions, the flash plug is coupled to the end cap, such that pivoting of the end cap from the closed position to the open position removes the flash plug from the cavity. In some versions, an interior surface of the cavity is coated with a fluid integrity preserving substance. In some versions, the fluid integrity preserving substance is heparin.

Another embodiment of the present disclosure provides a needle assembly that includes a color changing substance within the flashback chamber that changes color based on a characteristic of a fluid contained within the cavity, thereby automatically providing a visual indication of a condition of the patient. This embodiment includes an insertion needle and a needle hub. The insertion needle has a sharpened distal tip, a proximal end and a shaft defining a lumen extending therebetween. The needle hub is operably coupled to the proximal end of the insertion needle. The needle hub includes a flash chamber comprising a wall defining a cavity in fluid communication with the lumen of the insertion needle and sealed at one end by a gas permeable flash plug. The interior surface of the wall contains a color changing substance that changes color based on a characteristic of a fluid contained within the cavity, thereby providing a visual indication of a condition of the patient.

In some versions, the patient condition is at least one of glucose level, pregnancy, pH balance, and hormone level. In some versions, the flash chamber comprises transparent lateral walls for ease in viewing the color changing substance. In some versions, the interior surface is coated with two or more color changing substances that independently change color based on characteristics of a fluid contained within the cavity. In some versions, the two or more color changing substances change color based on different fluid characteristics. In some versions, the color changing substance is deposited on the interior surface in a pattern. In some versions, the pattern is at least one of a strip, a plurality of strips, a plurality of semi-spheres, a plurality of ovals, and a plurality of rhombuses. In some versions, the interior surface of the cavity is further coated with a reference color to which the color changing substance can be compared. In some versions, the interior surface of the cavity is further coated with a range of reference colors along a color spectrum to which the color changing substance can be compared. In some versions, the color changing substance is bonded to the interior surface of the cavity. In some versions, the color changing substance is adhered to one or more layers of fluid wicking material. In some versions, the needle assembly further includes a catheter that partially covers the insertion needle. In some versions, the needle assembly further includes a needle housing operably coupled to the needle hub, the needle housing moveable between a first position wherein the sharpened distal tip extends from the needle housing, and a second position wherein the sharpened distal tip is housed within the needle housing.

Another embodiment of the present disclosure provides a needle assembly that includes a flashback chamber that has a circumferential ring inserted therein that is coated with a color changing substance. This embodiment includes an insertion needle and a needle hub. The insertion needle has a sharpened distal tip, a proximal end and a shaft defining a lumen extending therebetween. The needle hub is operably coupled to the proximal end of the insertion needle. The needle hub includes a flash chamber comprising a wall defining a cavity in fluid communication with the lumen of the insertion needle and sealed at one end by a gas permeable flash plug. The flash plug is coated with a substance that changes color based on a characteristic of a fluid contained within the cavity, thereby providing a visual indication of a condition of the patient.

In some versions, the flash plug has a distal tapered nose and the color changing substance is deposited on the distal tapered nose. In some versions, the flash plug has a reduced diameter portion and the color changing substance is deposited on the reduced diameter portion.

Another embodiment of the present disclosure provides a needle assembly that includes a gas permeable flash plug coated with a color changing substance. This embodiment includes an insertion needle, a needle hub, and a circumferential ring. The insertion needle has a sharpened distal tip, a proximal end and a shaft defining a lumen extending therebetween. The needle hub is operably coupled to the proximal end of the insertion needle. The needle hub includes a flash chamber comprising a wall defining a cavity in fluid communication with the lumen of the insertion needle and sealed at one end by a gas permeable flash plug. The cavity defining wall further defines a circumferential groove positioned between the needle and the flash plug. The circumferential ring fits within the circumferential groove, and includes a substance that changes color based on a characteristic of a fluid contained within the cavity, thereby providing a visual indication of a condition of the patient.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 1 is a perspective view depicting a peripheral intravenous catheter of the prior art in a first position.

FIG. 2 is a perspective view depicting the peripheral intravenous catheter of FIG. 1 in a second position.

FIG. 3 is a perspective view depicting a first embodiment of a safety needle assembly in a first position in accordance with the disclosure.

FIG. 4 is a perspective view depicting the safety needle assembly of FIG. 3 in a second position.

FIG. 5 is cross sectional view depicting the safety needle assembly of FIG. 3.

FIGS. 6A-C depict views of a needle hub in accordance with embodiments of the disclosure.

FIG. 7 is a perspective view depicting the interaction between a needle hub and a needle housing in accordance with embodiments of the disclosure in a first position.

FIG. 8 is a perspective view depicting the interaction between the needle hub and the needle housing of FIG. 7 in a second position.

FIG. 9 is a perspective view depicting a second embodiment of a safety needle assembly in a first position in accordance with the disclosure.

FIG. 10 is a perspective view depicting the safety needle assembly of FIG. 9 in a second position.

FIG. 11 is a perspective view depicting a third embodiment of a safety needle assembly in accordance with the disclosure.

FIG. 12 is a perspective view depicting a fourth embodiment of a safety needle assembly in accordance with the disclosure.

FIGS. 13A-B are cross sectional views depicting a fifth embodiment of a safety needle assembly in accordance with the disclosure.

FIG. 16 is a perspective view depicting an eighth embodiment of a safety needle assembly in accordance with the disclosure.

FIGS. 17-18 depict the safety needle assembly of FIG. 16 with the end cap in an open position.

FIG. 19 is a perspective view depicting a ninth embodiment of a safety needle assembly in accordance with the disclosure.

FIG. 20 is a perspective view depicting a tenth embodiment of a safety needle assembly in accordance with the disclosure.

FIG. 22 depicts a flash chamber with a tapered nose flash plug in accordance with the disclosure.

FIG. 23 depicts a flash chamber with a stepped nose flash plug in accordance with the disclosure.

FIGS. 24-27 depict a flash chamber having patterns of one or more color changing substances applied to the interior of the flash chamber cavity defining wall in accordance with the disclosure.

Figure 14A:
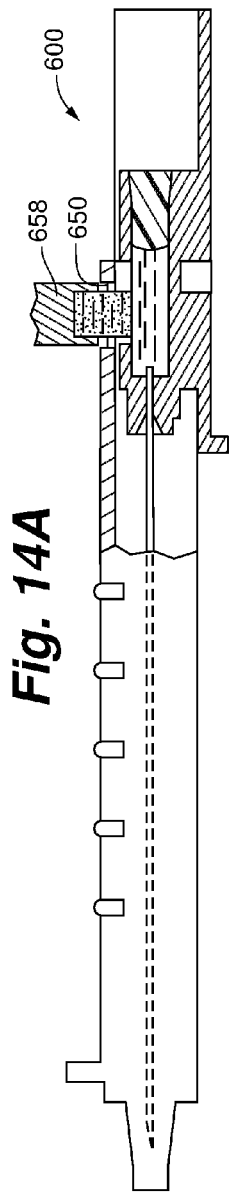
FIGS. 14A-B are cross sectional views depicting a sixth embodiment of a safety needle assembly in accordance with the disclosure.
Figure 14B:
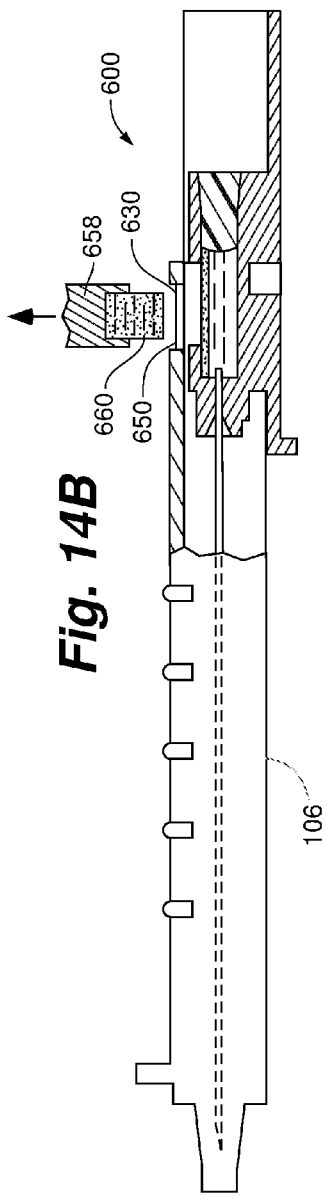

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Referring to FIGS. 1 and 2, a safety needle assembly 20 according to the prior art is depicted. Details of the safety needle assembly 20 are described in the Background section above.

A. First Embodiment

Referring to FIGS. 3-8, a safety needle assembly 100 according to a first embodiment of the disclosure is depicted. Safety needle assembly 100 can include an insertion needle 102, a needle hub 104, and a needle housing 106. Insertion needle 102 can have a sharpened distal tip 108, a proximal end 110 and a shaft 112 defining a lumen 114 extending therebetween.

Needle hub 104 can be operably coupled to the proximal end 110 of the insertion needle 102. As depicted in FIGS. 5 and 6A-C, the needle hub 104 can include a flash chamber 116 comprising a wall 118 defining a cavity 120. In one version, the cavity defining wall 118 can be constructed of a transparent or translucent material to enable a clinician to visually see when fluid enters the cavity 120.

The cavity 120 can be in fluid communication with the lumen 114 of the insertion needle 102. For example, in one version, the distal end 124 of the flash chamber 116 can include an aperture 126 sized to accommodate the proximal end 110 of the insertion needle 102. The cavity 120 can be sealed by a gas permeable flash plug 122. For example, in one version, the proximal end 128 of cavity 120 can be plugged with a microporous flash plug 122. Flash plug 122 can be comprised of a material that enables air to vent from the cavity 120 as fluid fills the cavity 120, while inhibiting the fluid from passing through the flash plug 122 and out of the cavity 120.

In one version, the flash chamber 116 can include a diagnostic sampling port 130. Diagnostic sampling port 130 can be configured to selectively provide a clinician access to fluid trapped in the cavity 120. In one version, the diagnostic sampling port 130 can be positioned on the wall 118 between the needle 102 and the flash plug 122. Because the internal diameter of the cavity 120 is generally smaller than the length of the cavity 120, locating diagnostic sampling port 130 generally orthogonal to the lumen 114 of the insertion needle 102 provides the advantage of enabling greater access to cavity 120. For example, an access port 150 positioned along the wall 118 can be sized to accommodate a standard sized blood glucose test strip, whereas such a standard sized blood glucose test strip may not fit within the internal diameter of cavity 120 if the diagnostic sampling port 130 is positioned on the proximal end 128 of cavity 120, or if it is included as part of the flash plug 122. Additionally, positioning diagnostic sampling port 130 along wall 118 does not cause any interference with the proper venting of flash plug 122.

In one version, diagnostic sampling port 130 can comprise a self-sealing member 133. Self-sealing member 133 can be, for example, constructed of silicone rubber. In some versions, for the purpose of preserving the integrity of the fluid trapped within cavity 120, the interior of flash chamber 116 can be coated with fluid integrity preserving substance, such as heparin.

Needle housing 106 has a distal end 132 and a proximal end 134. Distal end 132 of needle housing 106 can be configured with a tapered blunt tip sized to create a friction fit with a portion of a catheter hub 30. Distal end 132 can further define an aperture 140 through which insertion needle 102 can pass. In some versions, safety needle assembly 100 can include a catheter hub coupling and release mechanism configured to couple to the catheter hub in the first position, and release from the catheter hub 30 in the second position. Various catheter hub coupling and release mechanisms are disclosed in a concurrently filed application entitled "Releaseable Catheter Hub Retainer," Ser. No. 15/012,013, which is incorporated by reference herein.

Needle housing 106 can be slideably coupled to the needle hub 104. For example, in one version, needle hub 104 can have a "C" shaped cross section 142 conformed to fit around the outer surface of the needle housing 106 in a manner that inhibits the needle hub 104 from readily separating from the needle housing 106, yet enables the needle hub 104 to slide along the longitudinal axis of the needle housing 106 with minimal resistance. In a further version, the needle housing 106 can include structure defining a groove 144, and the needle hub 104 can be configured to slide along the groove 144, thereby inhibiting the needle hub 104 from rotating about the longitudinal axis of the needle housing 106. In one version, the needle hub 104 can include a lug 146 configured to fit within the groove 144 of the needle housing 106, thereby enabling linear movement of the needle hub 104 substantially parallel to the longitudinal axis of the needle housing 106, but restricting rotational movement of the needle hub 104 relative to the needle housing 106.

Needle housing 106 can be moveable between a first position (as depicted in FIGS. 3 and 7), wherein the sharpened distal tip 108 extends from the needle housing 106, and a second position (as depicted in FIGS. 4 and 8), wherein the sharpened distal tip 108 is housed within the needle housing 106. In the first position, when a catheter 22 is operably coupled to needle housing 106, a portion of insertion needle 102 can extend through aperture 140, and catheter 22, such that the sharpened distal tip 108 of insertion needle 102 protrudes slightly from catheter 22. In the second position, insertion needle 102 is withdrawn from catheter 22 and sharpened distal tip 108 is housed by needle housing 106 in a manner intended to reduce or eliminate the likelihood of an inadvertent needle stick.

In one version, the insertion needle 102 can be locked in position relative to needle housing 106. Several different types of locking mechanisms can be used for this purpose. For example, in one version, the structure of the needle housing 106 defining the groove 144 can further define a bottleneck 148, wherein the bottleneck 148 generally has a narrower width than the groove 144. Lug 146 of the needle hub 104 can be triangular or wedge-like in shape where the apex of the wedge faces the bottleneck 148 when in the first position. When an external force is applied to the needle hub 104 in an effort to slide it into the second position, the apex of the wedge of lug 146 will come into contact with the bottleneck 148. Bottleneck 148, which can have a width narrower than that of the lug 146 will initially resist movement of the lug 146 through the bottleneck 148. However, with sufficient force the wedge-shape lug 146 will cause the bottleneck 148 to temporarily deform, thereby enabling the lug 146 to pass through the bottleneck 148. Thereafter the lug 146 will be unable to pass back through the bottleneck 148 in the opposite direction, and the insertion needle 102 will be locked in position relative to the needle housing 106.

The needle housing 106 can include structure defining an access port 150. Access port 150 can be sized to accommodate a standard sized blood glucose test strip. In some embodiments, the access port 150 is positioned in proximity to the proximal end 134 of the needle housing 106 to align with the diagnostic sampling port 130 when the needle housing 106 is in the second position. Positioning the access port 150 in this location enables a clinician to access fluid trapped within the cavity 120 of flash chamber 116 when the insertion needle 102 is safely secured in the second position, thereby reducing the risk of an inadvertent needle stick.

B. Second Embodiment

Referring to FIGS. 9 and 10, a safety needle assembly 200 according to a second embodiment of the disclosure is depicted. In this embodiment, the access port 250 can be positioned in proximity to the distal end 232 of needle housing 206 to align with the diagnostic sampling port 230 when the needle housing 206 is in the first position. Positioning access port 250 in this location enables diagnostic sampling port 230 to be housed within the needle housing 206 in the second position; thereby reducing the likelihood that fluid will spill from the cavity 220 of flash chamber 216 should diagnostic sampling port 230 leak or fail.

C. Third and Fourth Embodiments

Referring to FIGS. 11 and 12, safety needle assemblies 300 and 400 according to a third and fourth embodiment of the disclosure are depicted. Safety needle assemblies 300 and 400 can include removable sample vials 352, 452. In one version, the sample vial 352, 452 can be comprised of a tubular member 354, 454 that selectively couples to access port 350, 450. Tubular member 354, 454 can include a sample vial flash plug 356 to enable air to escape as sample vial 352, 452 fills with fluid. In some versions, the sample vial flash plug 356 can be used in place of or as a replacement for a flash plug positioned within the flash chamber.

In some versions, safety needle assemblies 300 and 400 can include at least one of a protective needle housing 380, 480, a self-contained antiseptic swab, and a tourniquet for treatment and/or preparation of a biological site of a patient. Various catheter insertion devices having protective needle housings, a self-contained antiseptic swabs, and/or tourniquets are disclosed in a concurrently filed application entitled "Antiseptic Sheath with Site Preparation Provisions," Ser. No. 15/012,032 which is incorporated by reference herein.

D. Fifth and Sixth Embodiments

Figure 15:
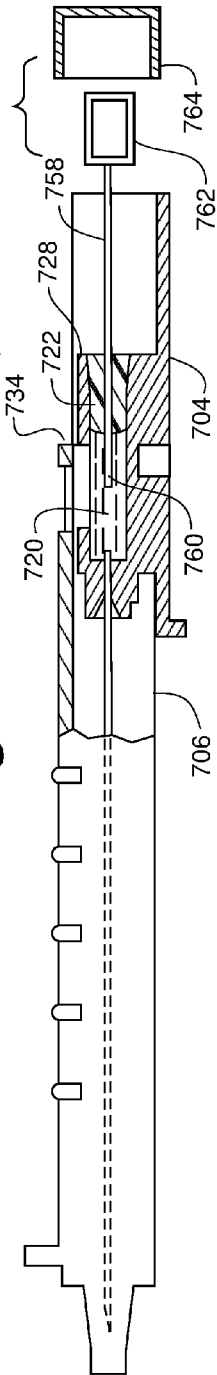
FIG. 15 is a cross sectional view depicting a seventh embodiment of a safety needle assembly in accordance with the disclosure.

Referring to FIGS. 13A-B and 14A-B, safety needle assemblies 500 and 600 according to a fifth and sixth embodiment of the disclosure are depicted. Safety needle assemblies 500 and 600 can include fluid sampling strips 558, 658, such as a blood glucose monitoring test strip or other similar test strip, device or mechanism, which can be pre-inserted into access port 550, 650 and/or diagnostic sampling port 530, 630. In one embodiment, fluid sampling strip 558, 658 includes a portion 560, 660 that is designed to collect fluid through capillary action, and another portion with electrical contacts (as depicted in FIG. 15) for connection with one or more fluid analyzers. In other embodiments, fluid sampling strip 558, 658 can begin as one color, such as white, and change color based on a chemical reaction with the fluid sample. In some embodiments, the fluid sampling strip 558, 658 is never removed from the safety needle assembly 500 or 600.

E. Seventh Embodiment

Referring to FIG. 15, a safety needle assembly 700 according to a seventh embodiment of the disclosure is depicted. In this embodiment, fluid sampling strip 758 can pass through flash plug 722 at the proximal end 728 of cavity 720. In this embodiment, fluid sampling strip 758 is rolled or sized to fit within the internal diameter of cavity 720. Electrical contacts 762 of the fluid sampling strip 758 can protrude from the proximal end 734 of needle housing 706 for connection with a fluid analyzer. In one embodiment, safety needle assembly 700 can include an end cap 764 that operably couples to needle housing 706 or needle hub 704 to selectively restrict access to electrical contacts 762. In one embodiment, the fluid sampling strip 758 can be fixedly coupled to the end cap 764 so that after the end cap 764 is removed from needle housing 706, the electrical contacts 762 can be connected with a fluid analyzer while safety needle assembly 700 can be safely disposed of.

F. Eighth Embodiment

Referring to FIG. 16-18, a safety needle assembly 800 according to an eighth embodiment of the disclosure is depicted. In this embodiment, an end cap 864 can be hingedly coupled to needle hub 804. For example, end cap 864 can be coupled to needle hub 804 via a pivotal coupling 866, such as a pivot, hinge or living hinge. In other embodiments, end cap 864 selectively couples to needle hub 804 though a friction or snap fitting. In some embodiments, end cap 864 further includes a latch 868 configured to secure one or both sides of end cap 864 to needle hub 804.

Where the end cap 864 is hingedly coupled to the needle hub 804, it can be moveable between a closed position (as depicted in FIG. 16), wherein the end cap 864 covers the cavity sealing flash plug 822, and an open position (as depicted in FIGS. 17 and 18), wherein the end cap 864 pivots to enable removal of the flash plug 822 from the cavity 820. Hingedly connecting end cap 864 to needle hub 804 offers the advantage of limiting the number of loose components to be discarded after use.

When the safety needle assembly 800 is in the first position, such that the sharpened distal tip of the insertion needle extends from the needle housing 806 (as depicted in FIG. 16), the needle housing 806 at least partially secures the end cap 864 in the closed position by inhibiting the end cap 864 from pivoting. For example, in some embodiments, the proximal end 834 of the needle housing 806 can extend within end cap 864 when in the first position, thereby inhibiting end cap 864 from pivoting. Securing end cap 864 in place when in the first position ensures that the insertion needle 802 is safely housed in the needle housing 806 before access to the fluid trapped in the flash chamber 816 is enabled, thereby reducing the chance of an inadvertent needle stick, while also inhibiting accidental fluid spillage by a premature release of the flash plug 822.

In one embodiment, the flash plug 822 can include a gripping surface 870 to aid in the removal of the flash plug 822 from the cavity 820. For example, gripping surface 870 can be a portion of flash plug 822 that extends beyond cavity 820. In one embodiment, gripping surface can include a lip or a loop for grasping. In one embodiment, flash plug 822 and end cap 864 are operably coupled to one another, such that removal of the end cap 864 causes the flash plug 822 to be removed from the cavity 820, thereby enabling access to the fluid trapped within the flash chamber 816.

G. Ninth and Tenth Embodiments

Referring to FIGS. 19-27, a needle assembly 900 end a safety needle assembly 1000 according to a ninth and tenth embodiment of the disclosure are depicted. These embodiments can include one or more color changing substances 972, 1072 that change color based on one or more characteristics of a fluid contained within cavity 920, 1020, thereby providing a visual indication of the state or condition of the patient. For example, in one embodiment, the color changing substance 972, 1072 changes color based on the presence or amount of one or more constituents, such as glucose, cardiac enzymes, red cells, hormone level, or the level of one or more than one parameter, such as pH. For these embodiments, needle assembly 900 or safety needle assembly 1000 can comprise a variety of needle assemblies, needle housing or otherwise, provided that the needle assembly includes a flash chamber 916, 1016.

Figure 21A:
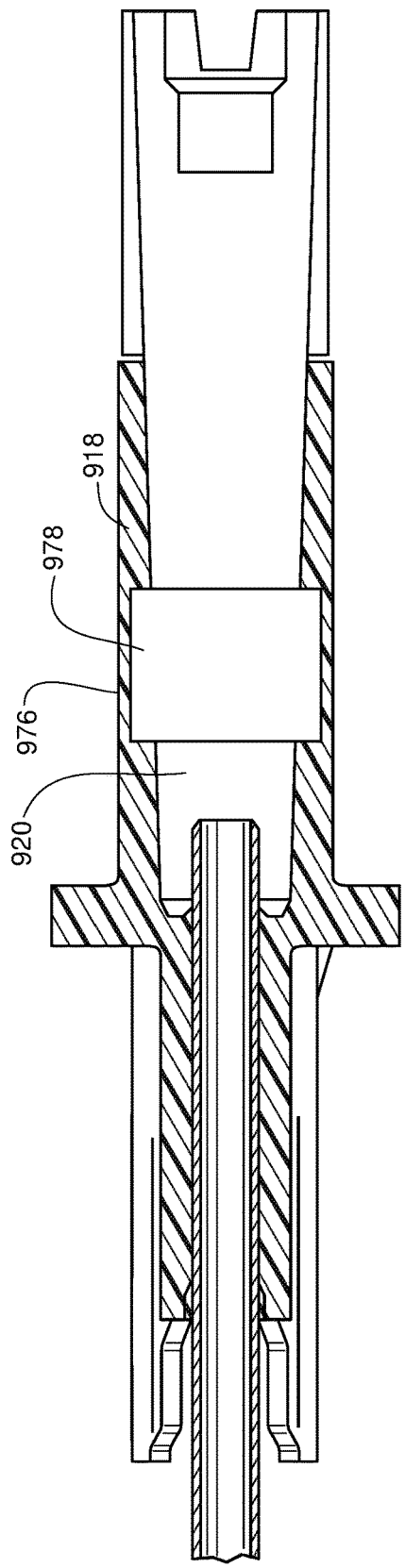
FIGS. 21A-B depict a flash chamber having a circumferential groove and ring in accordance with the disclosure.
Figure 21B:
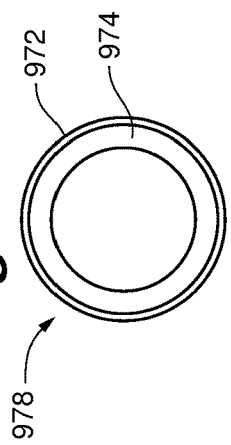

The color changing substance 972, 1072 can be bonded to the interior surface of the cavity 920, 1020. Referring to FIGS. 21A-B, in other embodiments, the color changing substance 972 is adhered to one or more layers of fluid wicking material 974. For increased visibility of the color changing substance 972 in opaque fluids, the fluid wicking material 974 can be in close proximity to the cavity defining wall 918 to reduce the amount of fluid between the color changing substance 972 and the inner surface of the cavity defining wall 918.

In one embodiment, the cavity defining wall 918 further defines a circumferential groove 976 positioned between the distal end and the proximal end of the cavity 920. A circumferential ring 978 including a color changing substance 972 can be positioned within the circumferential groove 976. In one embodiment, circumferential ring 978 can be comprised of a fluid wicking material 974 that wicks fluid toward the color changing substance 972 positioned in close proximity to the cavity defining wall 918. In another embodiment, circumferential ring 978 can be an o-ring coated with a color changing substance 972.

Referring to FIGS. 22-23, in some embodiments, the flash plug 922 is coated with a color changing substance 972. To ensure proper fluid contact on the color changing substance 972, while ensuring visibility of the color changing substance 972, flash plug 922 can have a distal tapered nose 982 or a reduced diameter or stepped nose 984 to which the color changing substance 972 is adhered or deposited. In some embodiments, the length of the flash plug 922 can be increased to provide additional surface area for positioning of the color changing substance 972. In some embodiments, different regions on the surface of the flash plug (e.g., different steps, different circumferential areas, etc.) can be coated with different color changing substances 972A and 972B.

Referring to FIGS. 24-27, in some embodiments, the color changing substance 972, 1072 can be deposited on the interior surface of the cavity defining wall 918, 1018 in one or more patterns. For example, color changing substance 972, 1072 can be configured as one or more stripes, semispheres, ovals, rhombuses, or any other pattern including a company logo or trademark. In one embodiment, two or more color changing substances 972A and 972B change color based on different fluid characteristics. In one embodiment, the interior surface of the cavity 920, 1020 is further coated with a reference color 980, 1080 to which one or more color changing substances 972, 1072 can be compared. The interior surface of the cavity 920, 1020, or the exterior surface of flash plug 922, 1022, can further be coated with a range of reference colors 1080A-I along a color spectrum to which one or more color changing substances 1072 can be compared.

H. Operation

In operation, placement of the catheters described herein generally includes preparation of the biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about 50 mm to 75 mm distal to the site. The needle and catheter are introduced into the vein by inserting the bevel of the sharpened distal tip into the vein at about a 20-30 degree angle with the bevel facing up in order to pierce one wall of the vein. If successful, blood from the vein will flow through the lumen of the needle and into the flash chamber, thereby indicating that the vein has been entered. A clinician can proceed to access the blood within the flash chamber for testing in accordance with the above described embodiments at this time or anytime thereafter.

To finish placement, the safety catheter assembly is lowered towards the skin to decrease the entry angle, and the catheter is advanced slightly into the vein. The needle is loosened and the catheter is gently advanced farther up into the vein until the catheter hub of the catheter is against the biological site. The tourniquet is loosened and the needle is withdrawn from the catheter, as the needle hub is moved from the first position to the second position, so that needle is safely locked within needle housing. Infusion tubing can be secured to the catheter hub of the catheter. The catheter is secured to the biological site by gauze and adhesive tape.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A needle assembly for accessing fluid from a patient, comprising:
    an insertion needle having a sharpened distal tip, a proximal end and a shaft defining a lumen extending therebetween;
    a needle hub operably coupled to the proximal end of the insertion needle, the needle hub including a flash chamber comprising a wall defining a cavity and a circumferential groove positioned between a distal end and a proximal end of the cavity, the cavity in fluid communication with the lumen of the insertion needle and sealed at one end by a gas permeable flash plug; and
    a circumferential ring including a color changing substance that changes color based on a characteristic of a fluid contained within the cavity positioned within the circumferential groove, thereby providing a visual indication of a condition of the patient.

2. The needle assembly of claim 1, wherein the patient condition is at least one of glucose level, pregnancy, pH balance, and hormone level.

3. The needle assembly of claim 1, wherein the flash chamber comprises transparent lateral walls for ease in viewing the color changing substance.

4. The needle assembly of claim 1, wherein the circumferential ring includes two or more color changing substances that independently change color based on characteristics of a fluid contained within the cavity.

5. The needle assembly of claim 4, wherein the two or more color changing substances change color based on different fluid characteristics.

6. The needle assembly of claim 1, wherein the color changing substance is deposited on the circumferential ring in a pattern.

7. The needle assembly of claim 6, wherein the pattern is at least one of a strip, a plurality of strips, a plurality of semi-spheres, a plurality of ovals, and a plurality of rhombuses.

8. The needle assembly of claim 1, wherein the interior surface of the needle hub further includes a reference color to which the color changing substance can be compared.

9. The needle assembly of claim 8, wherein the needle hub further includes a range of reference colors along a color spectrum to which the color changing substance can be compared.

10. The needle assembly of claim 1, wherein the color changing substance is adhered to one or more layers of fluid wicking material.

11. The safety needle assembly of claim 1, further comprising a catheter that partially covers the insertion needle.

12. The needle assembly of claim 1, further comprising a needle housing operably coupled to the needle hub, the needle housing movable between a first position where in the sharpened distal tip extends from the needle housing, and a second position when the sharpened distal tip is housed within the needle housing.

13. A needle assembly for accessing fluid from a patient, comprising:
    an insertion needle having a sharpened distal tip, a proximal end and a shaft defining a lumen extending therebetween;
    a needle hub operably coupled to the proximal end of the insertion needle, the needle hub including a flash chamber comprising a wall defining a cavity, the cavity in fluid communication with the lumen of the insertion needle and sealed at one end by a gas permeable flash plug, wherein the flash plug includes a reduced diameter portion coated with a substance that changes color based on a characteristic of a fluid contained within the cavity such that the substance is positioned in close proximity to the cavity defining wall, thereby providing a visual indication of a condition of the patient.

14. The needle assembly of claim 13, wherein the flash plug is coated with a plurality of color changing substances that independently change color based on characteristics of a fluid contained within the cavity.

15. The needle assembly of claim 13, further comprising a needle housing operably coupled to the needle hub, the needle housing movable between a first position where in the sharpened distal tip extends from the needle housing, and a second position when the sharpened distal tip is housed within the needle housing.

* * * * *